United States Patent [19]

Redmon

[11] Patent Number: 5,445,145
[45] Date of Patent: Aug. 29, 1995

[54] APPARATUS TO MANUALLY OPEN AND CLOSE A SHUTTER-LIKE DEVICE FOR TRACHEOSTOMY PATIENTS TO FACILITATE BREATHING

[76] Inventor: Robert A. Redmon, 3005 Fondley Rd., Winston Salem, N.C. 27105

[21] Appl. No.: 324,796

[22] Filed: Oct. 18, 1994

[51] Int. Cl.$^6$ .............................................. A61M 16/00
[52] U.S. Cl. ................................ 128/207.16; 128/912
[58] Field of Search .................... 128/207.14, 207.15, 128/207.16, 912, 863, 887; 623/9

[56] References Cited

U.S. PATENT DOCUMENTS

| | | | |
|---|---|---|---|
| 2,039,142 | 4/1936 | Brehm | 623/9 |
| 2,198,241 | 4/1940 | Brehm | 623/9 |
| 3,137,299 | 6/1964 | Tabor | 623/9 |
| 3,263,684 | 8/1966 | Bolton | 623/9 |
| 3,952,335 | 4/1976 | Sorce et al. | 623/9 |
| 4,040,428 | 8/1977 | Clifford | 623/9 |
| 4,325,366 | 4/1982 | Tabor | 128/207.16 |
| 4,463,757 | 8/1984 | Schmidt | 128/205.29 |
| 4,582,058 | 4/1986 | Depel et al. | 128/207.16 |
| 4,809,693 | 3/1989 | Rangoni et al. | 623/9 |
| 5,022,394 | 6/1991 | Chmielinski | 128/207.14 |
| 5,054,484 | 10/1991 | Hebeler, Jr. | 128/207.14 |
| 5,059,208 | 10/1991 | Coe et al. | 623/9 |
| 5,107,828 | 4/1992 | Koss et al. | 128/207.16 |
| 5,160,322 | 11/1992 | Scheremet et al. | 128/887 |

FOREIGN PATENT DOCUMENTS 0389470  9/1908  France .................................... 623/9

Primary Examiner—Edgar S. Burr
Assistant Examiner—Aaron J. Lewis

[57] ABSTRACT

An apparatus to manually open and close a shutter-like device for tracheostomy patients to facilitate breathing comprises a shutter box positionable over a tracheostomy opening in the neck of a patient. The shutter box has slits on the exterior face and an aperture on the interior face and a control device with a closure surface pivotable between an open position to allow passage of air through the aperture and openings and a closed position over the aperture to preclude the flow of air therethrough. Motion imparting mechanisms include a pivot pin extending through the box and control device to allow the pivoting thereof and a securement pin on the side of the pivot pin remote from the closure surface to effect the rotational movement thereof.

4 Claims, 4 Drawing Sheets

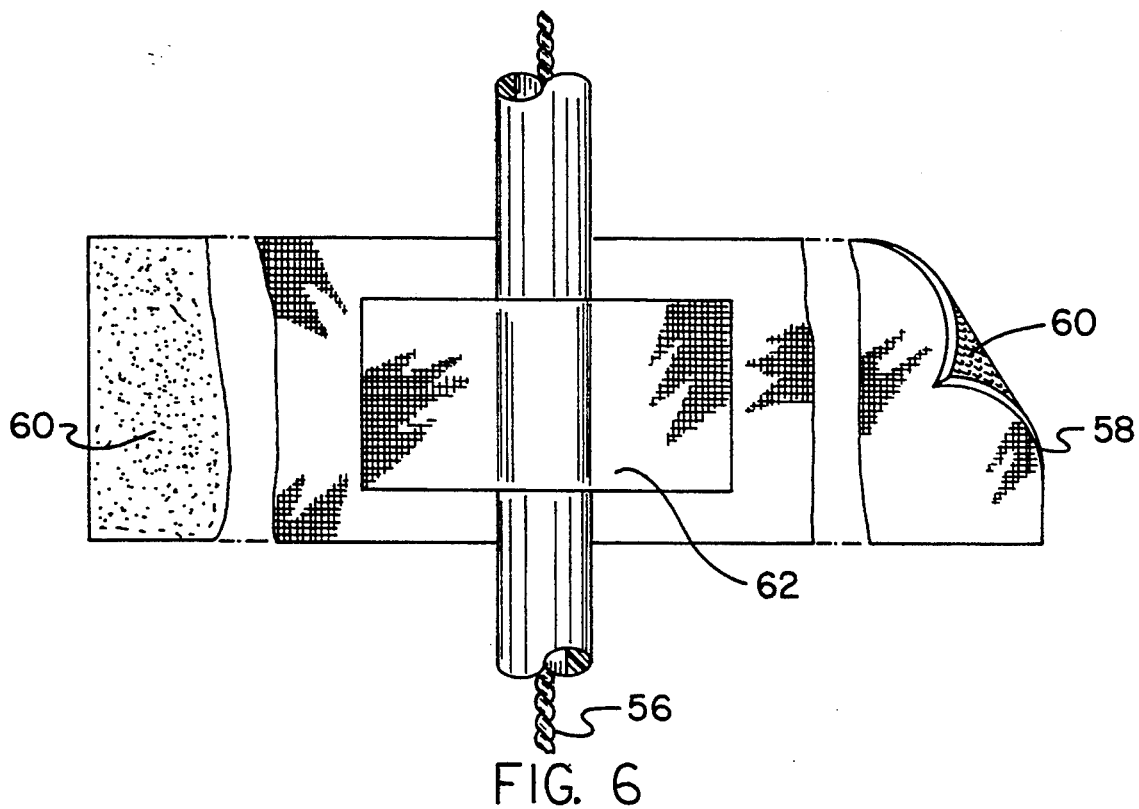
FIG. 6
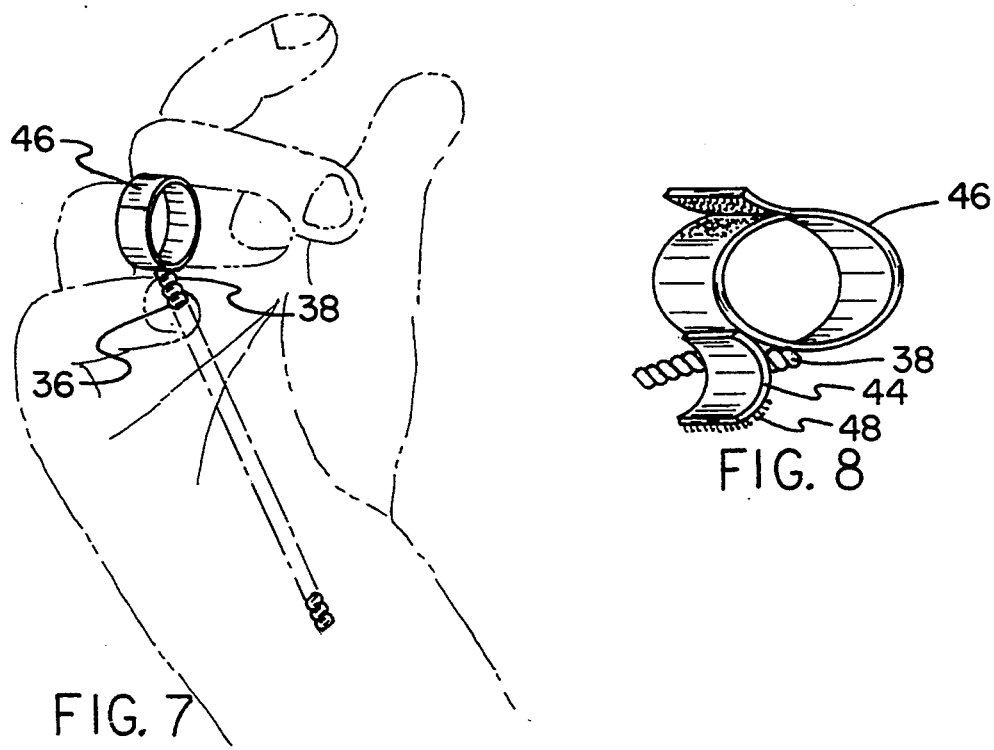
FIG. 7
FIG. 8

ND CLOSE
APPARATUS TO MANUALLY OPEN AND CLOSE A SHUTTER-LIKE DEVICE FOR TRACHEOSTOMY PATIENTS TO FACILITATE BREATHING

BACKGROUND OF THE INVENTION

1. Field of the Invention

The present invention relates to an apparatus to manually open and close a shutter-like device for tracheostomy patients to facilitate breathing and more particularly pertains to opening and closing a shutter in front of a tracheostomy opening to render breathing easier for patients.

2. Description of the Prior Art

The use of devices of various designs and configurations to open and close passage to a tracheostomy opening is known in the prior art. More specifically, devices of various designs and configurations to open and close passage to a tracheostomy opening heretofore devised and utilized for the purpose of assisting patients with tracheostomy openings by allowing them to manually open and close access to the opening for breathing purposes are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 5,107,828 to Koss a tracheostomy closure device.

U.S. Pat. No. 5,059,208 to Coe discloses an adjustable tracheostomy valve.

U.S. Pat. No. 5,054,484 to Hebeler discloses a tracheostomy device.

U.S. Pat. No. 4,582,058 to Depel discloses tracheostomy valves.

U.S. Pat. No. 4,325,366 to Tabor discloses valve and method for use with a tracheotomy tube.

In this respect, the apparatus to manually open and close a shutter-like device for tracheostomy patients to facilitate breathing according to the present invention substantially departs from the conventional concepts and designs of the prior art, and in so doing provides an apparatus primarily developed for the purpose of opening and closing a shutter in front of a tracheostomy opening to render breathing easier for patients.

Therefore, it can be appreciated that there exists a continuing need for an improved apparatus to manually open and close a shutter-like device for tracheostomy patients to facilitate breathing which can be used for opening and closing a shutter in front of a tracheostomy opening to render breathing easier for patients. In this regard, the present invention substantially fulfills this need.

SUMMARY OF THE INVENTION

In view of the foregoing disadvantages inherent in the known types of devices of various designs and configurations to open and close passage to a tracheostomy opening now present in the prior art, the present invention provides an improved apparatus to manually open and close a shutter-like device for tracheostomy patients to facilitate breathing. As such, the general purpose of the present invention, which will be described subsequently in greater detail, is to provide a new and improved apparatus to manually open and close a shutter-like device for tracheostomy patients to facilitate breathing apparatus and method which has all the advantages of the prior art and none of the disadvantages.

To attain this, the present invention essentially comprises an apparatus to manually open and close a shutter-like device for tracheostomy patients to facilitate breathing comprising a shutter box positionable over a tracheostomy opening in the neck of a patient. The shutter box has slits on the exterior face and a circular aperture on the interior face and a control device with a closure surface pivotable between an open position to allow passage of air through the aperture and slits and a closed position over the aperture to preclude the flow of air therethrough. Motion imparting mechanisms include a pivot pin extending through the box and control device to allow the pivoting thereof and a securement pin on the side of the pivot pin remote from the closure surface to effect the rotational movement thereof. A cable is attached to the securement pin and extends through an aperture of the shutter box remote, then down a patient's arm with a coupling component for removably securing the remote end of the cable to a patient's finger. The cable has associated therewith, a tube for encasing the cable over the majority of its length. A plurality of removably attachable securement straps with pile type fasteners associated therewith and a tube attachment mechanism are adapted to secure the tube for the cable thereadjacent whereby the tube and cable may be caused to follow a path of travel down a wearer's arm, whereby the movement of a wearer's finger with the remote end of the cable attached thereto will urge the upper end of the cable to act against the action of the spring to open the aperture through the rotation of the control device.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide an improved apparatus to manually open and close a shutter-like device for tracheostomy patients to facilitate breathing which has all the advantages of the prior art devices of various designs and configurations to open and close passage to a tracheostomy opening and none of the disadvantages.

It is another object of the present invention to provide a new apparatus to manually open and close a shutter-like device for tracheostomy patients to facilitate breathing which may be easily and efficiently manufactured and marketed.

It is a further object of the present invention to provide a new apparatus to manually open and close a shutter-like device for tracheostomy patients to facilitate breathing which is of a durable and reliable construction.

An even further object of the present invention is to provide a new apparatus to manually open and close a shutter-like device for tracheostomy patients to facilitate breathing which is susceptible of a low cost of manufacture with regard to both materials and labor, and which accordingly is then susceptible of low prices of sale to the consuming public, thereby making such devices of various designs and configurations to open and close passage to a tracheostomy opening economically available to the buying public.

Still yet another object of the present invention is to provide a new apparatus to manually open and close a shutter-like device for tracheostomy patients to facilitate breathing which provides in the apparatuses and methods of the prior art some of the advantages thereof, while simultaneously overcoming some of the disadvantages normally associated therewith.

Still another object of the present invention is to open and close a shutter in front of a tracheostomy opening to render breathing easier for patients Lastly, it is an object of the present invention to provide a new and improved apparatus to manually open and close a shutter-like device for tracheostomy patients to facilitate breathing comprising a shutter box positionable over a tracheostomy opening in the neck of a patient. The shutter box has slits on the exterior face and an aperture on the interior face and a control device with a closure surface pivotable between an open position to allow passage of air through the aperture and openings and a closed position over the aperture to preclude the flow of air therethrough. Motion imparting mechanisms include a pivot pin extending through the box and control device to allow the pivoting thereof and a securement pin on the side of the pivot pin remote from the closure surface to effect the rotational movement thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a front elevational view of a portion of the cable of the prior Figures with the associated mechanisms for coupling to a patient's arm.

FIG. 7 illustrates the coupling of a cable to a patient's hand.

FIG. 8 is a perspective illustration of the device for coupling the cable of the prior Figures to a wearer's hand.

Similar reference numerals refer to similar parts throughout the various Figures.

DESCRIPTION OF THE PREFERRED EMBODIMENT

Figure 1:
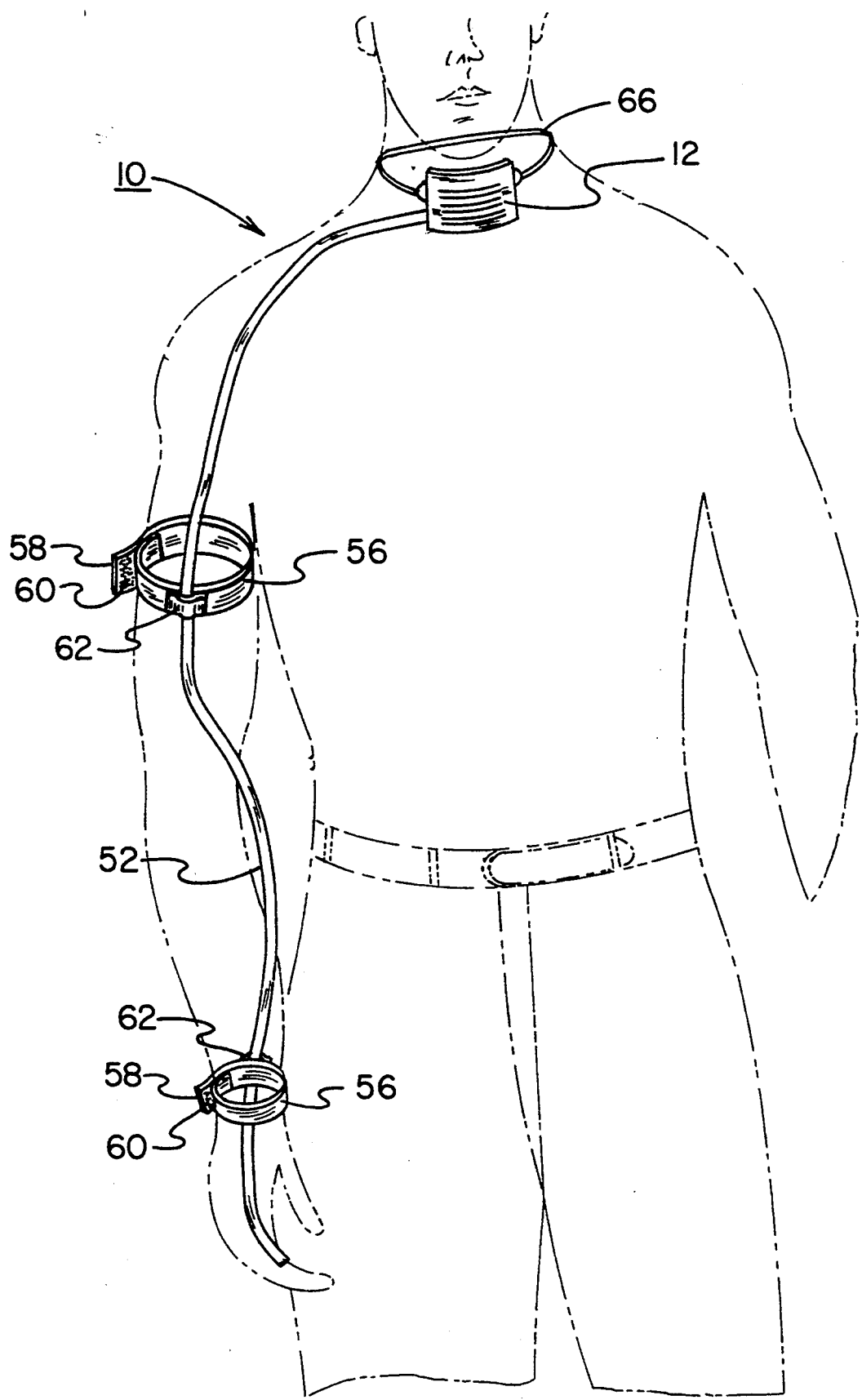
FIG. 1 is a perspective illustration of the preferred embodiment of the apparatus to manually open and close a shutter-like device for tracheostomy patients to facilitate breathing constructed in accordance with the principals of the present invention.
Figure 2:
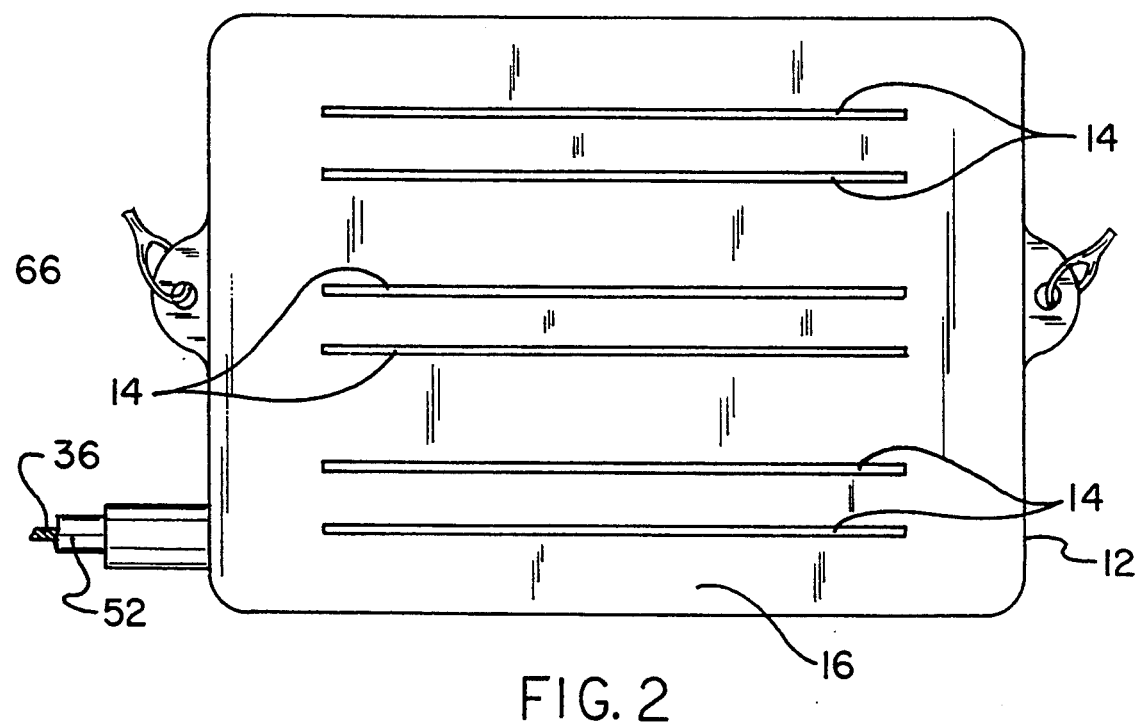
FIG. 2 is a front elevational view of the shutter device shown in FIG. 1.
Figure 3:
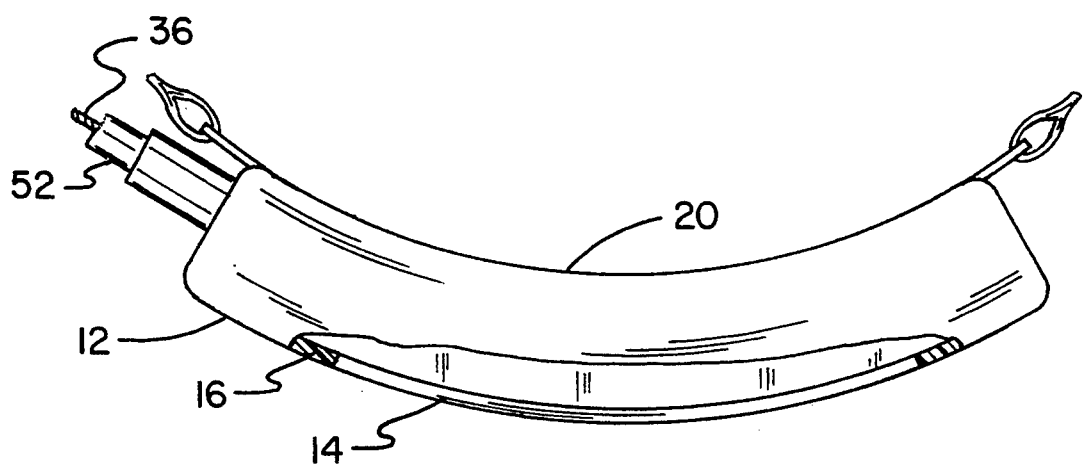
FIG. 3 is a top plan view of the device shown in FIG. 2.
Figure 4:
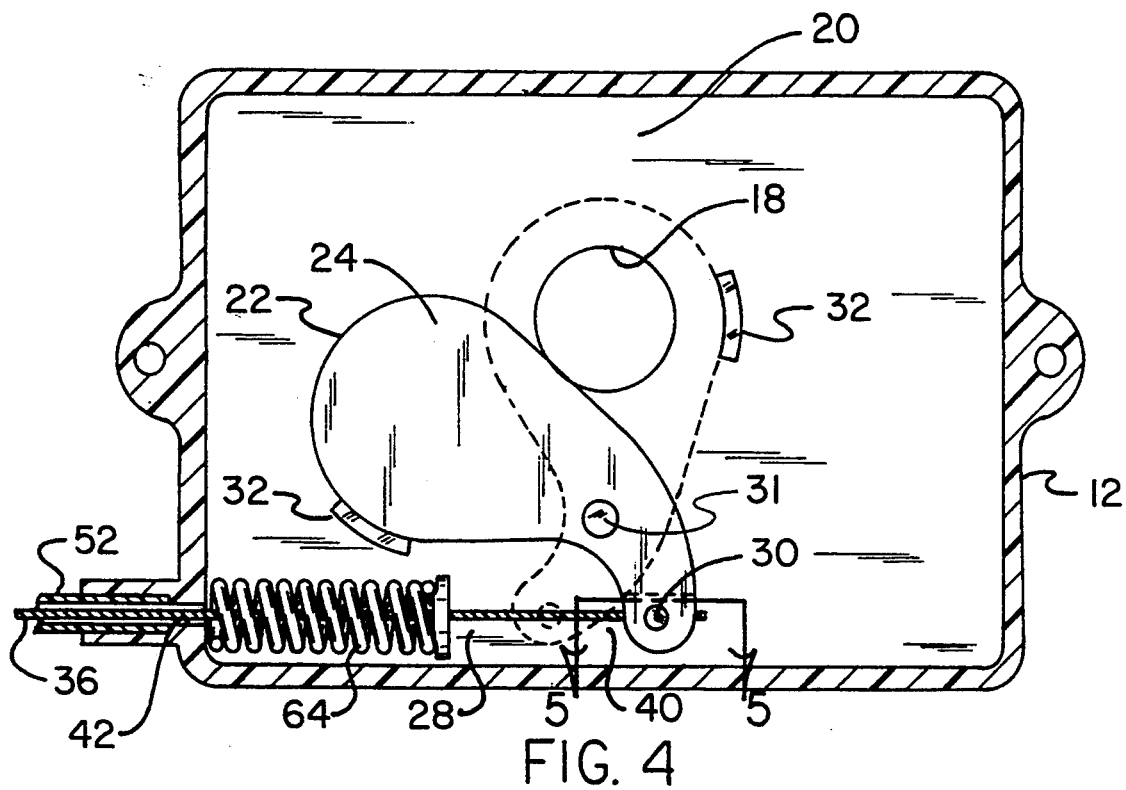
FIG. 4 is a cross sectional view of the device shown in FIG. 2.
Figure 5:
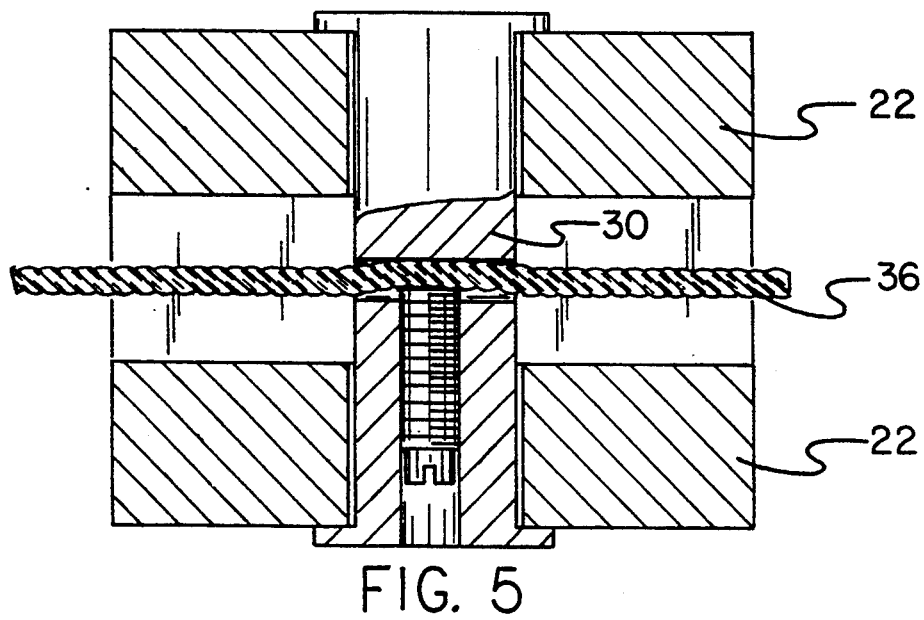
FIG. 5 is a cross-sectional view taken along line 5—5 of FIG. 4.

With reference now to the drawings, and in particular to FIG. 1 thereof, a new apparatus to manually open and close a shutter-like device for tracheostomy patients to facilitate breathing embodying the principles and concepts of the present invention and generally designated by the reference numeral 10 will be described.

The invention, the new and improved apparatus to manually open and close a shutter-like device for tracheostomy patients to facilitate breathing is comprised of a plurality of components. In their broadest context, such components include a shutter box, motion imparting mechanisms, a cable and securement straps. Such components are specifically configured and correlated with respect to each other so as to attain the desired objective.

The central component of the system 10 of the present invention is a shutter box 12. The shutter box is positionable over a tracheostomy opening in the neck of a patient. The shutter box has a plurality of slits 14 in the exterior face 16 of the shutter box. In addition, a circular aperture 18 is formed on the interior face 20 of the shutter box. In association therewith, a control device 22 with a closure surface 24 is pivotable between an open position to allow passage of air through the aperture and slits and a close position over the aperture and slits to preclude the flow of air therethrough.

Motion imparting mechanisms 28 are next provided. Such mechanisms include a pivot pin 31 extending through the box and the control device. Such pivot pin is to allow the pivoting of the control device between the open and closed position. Also included is a securement pin 31 secured to the control device on the side of the pivot pin remote from the closure surface. This is to effect the rotational movement thereof. Arcuate abutment surfaces 32 are next provided to limit the extent of rotation of the control device.

The next component of the system 10 is a cable 36. The cable has an interior secured end 38 and an exterior free end 40. The near end is attached through the securement pin. It then extends through an aperture 42 in the shutter box. The cable extends downwardly along a patient's arm. A coupling component 44 is then provided for removable securement of the remote free end of the cable to the patient's finger. A flexible ring 46 with a pile type fastener 48 at its end allows for the adjustable securement to a wearer's finger as a function of the size of such finger.

The cable has an association therewith a tube 52. The tube is of a length nearly as long as the cable but allowing the cable to extend exteriorly of the tube. The tube functions for encasing the cable which is slidably received over the majority of its length.

The last component of the system is a plurality of removably attachable securement straps 56. Each such strap is provided with free ends 58 and a pile type fastener 60 secured with respect to such free ends. A tube attachment mechanism 62 again in the form of a strip with pile type fasteners for coupling purposes, is adapted to secure the tube for the cable thereadjacent. In this manner, the tube and cable may be caused to follow a path of travel down a wearer's arm. In this manner, the movement of a wearer's finger with the remote end of the cable attached thereto will urge the other end of the cable to reciprocate and act against the action of a spring 64 to open the aperture through the rotation of the control device. A flexible strap 66 is also provided to hold the shutter box and associated components in proper positioning adjacent to the tracheostomy opening on the wearer's neck.

The present invention relates to the opening which is made in the trachea, or windpipe, to improve the breathing of people who are having difficulty in drawing in an adequate amount of air into their lungs. Tracheostomies to place the opening in the windpipe are performed for various reasons, including obstructions that are caused by swelling from inflammations or objects which have become lodged. Some surgery also results in the performance of a tracheostomy. A skin incision is made, followed by a short longitudinal incision in the trachea inferior to the cricoid cartilage. The patient breathes through a tube, or through a shutter-like device which is placed in the opening. Some patients have no difficulty with this arrangement, but others find it rather difficult to exhale.

This invention attaches the shutter to a push/pull cable mechanism which extends down the arm so it can be opened and closed by the fingers. The shutter can be spring loaded to close, with a slight pull on the cable required to open it. Slack is provided in the unit so the shutter can be removed easily for cleaning. The cable housing is strapped to the arm so it does not flex when the wire it contains is pushed or pulled.

The tracheostomy mechanism enables the person to control the opening rather than attempting to blow it open. When a person is in a weakened condition or has lost some of the flexibility in the lungs, this device increases their confidence and reassures them that they need not experience difficulty in breathing. The components are made of plastic and stainless steel.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An apparatus to manually open and close a shutter device for tracheostomy patients to facilitate breathing comprising, in combination:

a shutter box positionable over a tracheostomy opening in the neck of a patient, the shutter box having slits on the exterior face and a circular aperture on the interior face and a control device with a closure surface pivotable between an open position to allow passage of air through the aperture and slits and a closed position over the aperture to preclude the flow of air therethrough;

motion imparting mechanisms including a pivot pin extending through the box and control device to allow the pivoting thereof and a securement pin on the side of the pivot pin remote from the closure surface to effect rotational movement of the control device, abutment surfaces are provided to limit the extent of rotation of the control device between the open and close position;

a cable attached to the securement pin and extending through an aperture of the shutter box remote, then down a patient's arm with a coupling component for removably securing the remote end of the cable to a patient's finger, the cable having associated therewith, a tube for encasing the cable over the majority of its length; and a plurality of removably attachable securement straps with pile type fasteners associated therewith and a tube attachment mechanism adapted to secure the tube for the cable thereadjacent whereby the tube and cable may be caused to follow a path of travel down a wearer's arm, whereby the movement of a wearer's finger with the remote end of the cable attached thereto, will urge the upper end of the cable to act against the action of the spring to open the aperture through the rotation of the control device.

2. An apparatus to manually open and close a shutter device for tracheostomy patients to facilitate breathing comprising:

a shutter box positionable over a tracheostomy opening in the neck of a patient, the shutter box having slits on the exterior face and an aperture on the interior face and a control device with a closure surface pivotable between an open position to allow passage of air through the aperture and openings and a closed position over the aperture to preclude the flow of air therethrough; and motion imparting mechanisms including a pivot pin extending through the box and control device to allow the pivoting thereof and a securement pin on the side of the pivot pin remote from the closure surface to effect rotational movement of the control device.

3. The apparatus as set forth in claim 2 and further including:

a cable attached to the securement pin and extending through an aperture of the shutter box remote, then down a patient's arm with a coupling component for removably securing the remote end of the cable to a patient's finger, the cable having associated therewith, a tube for encasing the cable over the majority of its length.

4. The apparatus as set forth in claim 2 and further including:

a plurality of removably attachable securement straps with pile type fasteners associated therewith and a tube attachment mechanism adapted to secure the tube for the cable thereadjacent whereby the tube and cable may be caused to follow a path of travel down a wearer's arm, whereby the movement of a wearer's finger with the remote end of the cable attached thereto, will urge the upper end of the cable to act against the action of the spring to open the aperture through rotation of the control device.

* * * * *